United States Patent
Johnson et al.

(10) Patent No.: US 12,350,104 B2
(45) Date of Patent: Jul. 8, 2025

(54) SYSTEMS AND METHODS FOR CONTROLLING VOLUME RATE

(71) Applicant: KONINKLIJKE PHILIPS N.V., Eindhoven (NL)

(72) Inventors: Keith William Johnson, Lynwood, WA (US); Anne Holmes, Bothell, WA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 107 days.

(21) Appl. No.: 17/606,853

(22) PCT Filed: May 5, 2020

(86) PCT No.: PCT/EP2020/062397
§ 371 (c)(1),
(2) Date: Oct. 27, 2021

(87) PCT Pub. No.: WO2020/225240
PCT Pub. Date: Nov. 12, 2020

(65) Prior Publication Data
US 2022/0233171 A1    Jul. 28, 2022

Related U.S. Application Data

(60) Provisional application No. 62/843,718, filed on May 6, 2019.

(51) Int. Cl.
*A61B 8/08* (2006.01)
*A61B 8/00* (2006.01)

(52) U.S. Cl.
CPC .............. *A61B 8/483* (2013.01); *A61B 8/469* (2013.01); *A61B 8/5207* (2013.01); *A61B 8/5292* (2013.01); *A61B 8/54* (2013.01); *A61B 8/585* (2013.01)

(58) Field of Classification Search
CPC ....... A61B 8/483; A61B 8/469; A61B 8/5207; A61B 8/5292; A61B 8/54; A61B 8/585
See application file for complete search history.

(56) References Cited

U.S. PATENT DOCUMENTS

| | | |
|---|---|---|
| 2004/0064048 A1 | 4/2004 | Li |
| 2005/0096553 A1 | 5/2005 | Chomas et al. |
| 2005/0228280 A1 | 10/2005 | Ustuner et al. |
| 2005/0283079 A1 | 12/2005 | Steen et al. |
| 2014/0358006 A1 | 12/2014 | Snyder et al. |

(Continued)

OTHER PUBLICATIONS

ISR & Written Opinion, Jul. 17, 2020.

(Continued)

*Primary Examiner* — Anne M Kozak
*Assistant Examiner* — Kaitlyn E Sebastian

(57) ABSTRACT

The present disclosure describes systems and methods for determining if a feature of interest is present in a volume or plane scanned by an imaging system. In examples, one or more imaging planes are analyzed for anatomical landmarks to determine whether a feature of interest is present. If the feature of interest is present, scan parameters may be determined to scan an adjusted volume that includes the feature of interest. In some applications, the adjusted volume may allow the imaging system to increase a volume rate.

17 Claims, 9 Drawing Sheets

(56) References Cited

U.S. PATENT DOCUMENTS

| | | |
|---|---|---|
| 2015/0011886 A1 | 1/2015 | Radulescu et al. |
| 2016/0262720 A1* | 9/2016 | Henderson et al. |
| 2016/0287214 A1* | 10/2016 | Ralovich ............... A61B 8/469 |
| 2017/0053396 A1* | 2/2017 | Zhai ...................... A61B 8/467 |
| 2020/0174118 A1* | 6/2020 | Tadross ................ A61B 8/0891 |
| 2020/0226422 A1* | 7/2020 | Li ............................ G06N 3/04 |

OTHER PUBLICATIONS

Krizhevsky et al: "Imagenet Classification With Deep Convolutional Neural Networks"; Communications of the ACM, Jun. 2017, vol. 60, No. 6, pp. 84-90.

* cited by examiner

SYSTEMS AND METHODS FOR CONTROLLING VOLUME RATE

CROSS-REFERENCE TO PRIOR APPLICATIONS

This application is the U.S. National Phase application under 35 U.S.C. § 371 of International Application No. PCT/EP2020/062397, filed on May 5, 2020, which claims the benefit U.S. Provisional Patent Application 62/843,718, filed on May 6, 2019. These applications are hereby incorporated by reference herein.

TECHNICAL FIELD

The present disclosure pertains to imaging systems and methods for controlling the volume rate during real-time ultrasound imaging. Particular implementations involve systems configured to adjust sector width and/or number of elevational planes based on anatomical landmarks to control the volume rate.

BACKGROUND

During ultrasound imaging, multiple planes in a volume may be scanned by an ultrasound transducer array. The multiple planes may be used to generate a three-dimensional (3D) data set. The 3D data set may be processed by a multiplanar reformatter, which reconstructs slices from the 3D data set to provide 2D ultrasound images for viewing. The slices to be reconstructed may be determined by a user or an ultrasound imaging system. The 3D data set may be processed by a volume renderer, which may reconstruct the 3D data set into a 3D image for viewing. Both 2D and 3D ultrasound images generated from the 3D data set may be displayed concurrently. The 2D and 3D images may be displayed at or near real time. However, as the volume scanned gets larger and/or the desired resolution increases, the volume rate (e.g. the rate at which the volume is scanned) of the transducer array may decrease. This may decrease the ability of the multiplanar reformatter to provide real time 2D images and/or the volume renderer to provide real time 3D images.

SUMMARY

The present disclosure describes systems and methods to control the volume rate at a clinically relevant level by controlling the number of elevational planes and lines per plane (e.g., sector width) acquired based on landmarks within the field of acquisition. For example, systems and methods are provided for obtaining orthogonal plane data to identify landmarks, and use those landmarks to identify a more optimal elevational angle from the defaulted angle, which may minimize the amount of data required for the volume and thus allow for increased volume rate.

In accordance with examples of the present disclosure, an ultrasound imaging system may include an ultrasound sensor array configured to scan at least one plane in a region, a signal processor configured to generate at least one image frame from the at least one plane, a data processor in communication with the signal processor, wherein the data processor include a neural network configured to receive the at least one image frame, wherein the neural network is trained to determine whether a feature of interest is present in the at least one image frame, wherein the neural network is further configured, upon determination that the feature of interest is present in the at least one image frame, to output boundary data for the feature of interest, and an acquisition controller configured to receive the boundary data, generate, using the boundary data, scan parameters corresponding to a volume including the feature of interest, and a beamformer in communication with the data processor, wherein the beamformer is configured to receive the scan parameters and cause the ultrasound sensor array to perform subsequent scanning of the volume including the feature of interest in accordance with the scan parameters.

In accordance with examples of the present disclosure, a method may include scanning, with an ultrasound sensor array, at least one plane in a region, generating at least one image frame from the at least one plane, analyzing, with a neural network of a data processor, the at least one image frame to determine if a feature of interest is present, if the feature of interest is determined to be present, generating, with the neural network, boundary data for the feature of interest, if the feature of interest is determined to be present, generating, with an acquisition controller of the data processor, scan parameters corresponding to a volume that includes the feature of interest, based at least in part on the boundary data; and scanning, with the ultrasound sensor array, the volume.

Any of the methods described herein, or steps thereof, may be embodied in non-transitory computer-readable medium comprising executable instructions, which when executed may cause a processor of a medical imaging system to perform the method or steps embodied herein.

DETAILED DESCRIPTION

Figure 1:
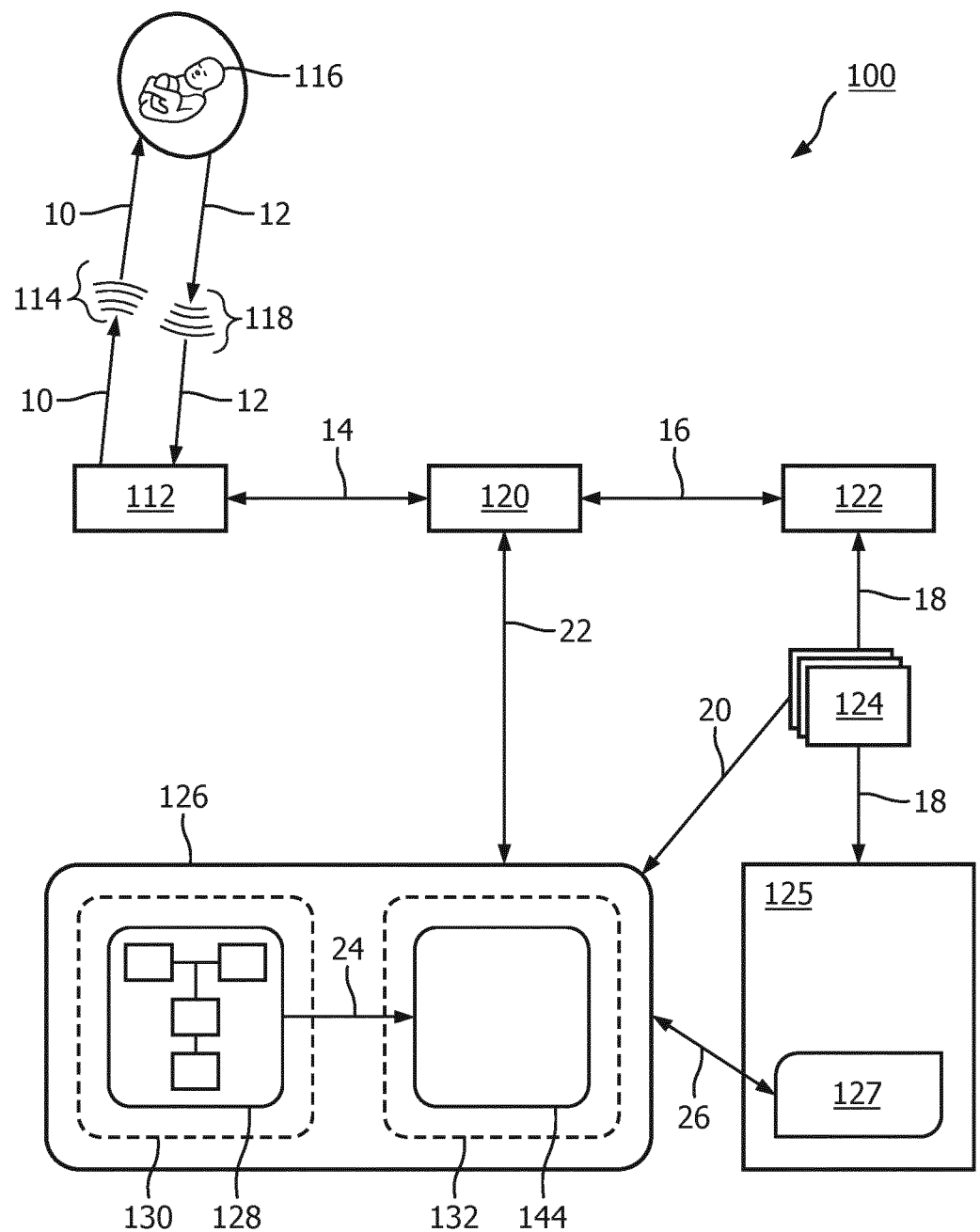
FIG. 1 is a block diagram of an ultrasound system in accordance with examples described herein.

The following description of certain embodiments is merely exemplary in nature and is in no way intended to limit the invention or its applications or uses. In the following detailed description of embodiments of the present systems and methods, reference is made to the accompanying drawings which form a part hereof, and which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

An ultrasound imaging system user may scan a volume with an ultrasound transducer array searching for features of interest by transmitting and receiving ultrasound signals. For example, the user may search for a fetal heart within a fetus or a carotid artery in a neck. A volume is scanned by acquiring ultrasound signals corresponding to a number of spaced two-dimensional imaging planes (e.g., elevational planes). The imaging planes, sometimes referred to simply as planes, may be spaced at regular intervals, that is, a distance between centers of any two planes is the same for the entire volume. The angle between planes at either end of a set of planes may be referred to the elevational angle. If the spacing of the planes is kept constant, the elevational angle determines a number of imaging planes acquired. Each plane includes a number of scan lines, which may also be regularly spaced. If the density of scan lines is held constant, the number of lines in a plane may determine a width of the plane, referred to as the sector width. The more imaging planes and/or greater the sector width, the longer it may take to scan the volume. That is, it lowers volume rate. The number of imaging planes, elevational angle, scan line density, number of scan lines, and/or sector width are examples of scan parameters.

Often, the initial volume scanned is larger than a volume of the feature of interest. This may reduce the difficulty of finding the feature of interest in an object. However, scanning a larger volume may decrease the volume rate of the transducer array. This may limit the user's ability to view the feature of interest in real time. For example, in some instances, the fetal heart rate may be faster than the volume rate of the transducer array. Once a feature of interest is found, a user may adjust scan parameters such as the number of imaging planes and/or the number of lines in each plane (e.g., sector width) to scan an adjusted volume that more closely matches the volume of the feature of interest. In some applications, this may increase volume rate by reducing the volume scanned. However, adjusting these parameters manually is cumbersome and time consuming. Furthermore, some users, especially those with less experience, may inadvertently cause the feature of interest to fall outside the scanned volume while attempting to control the volume rate.

An ultrasound imaging system disclosed herein may automatically detect features of interest, and based on the feature of interest detected, adjust a number of imaging planes and/or sector width to adjust the volume scanned to control the volume rate. In some applications, rather than adjusting an initial volume scanned, the ultrasound imaging system may determine a volume to scan based on one or more 2D planes acquired that include a feature of interest. Automatically adjusting and/or setting the volume to be scanned may reduce the time the user spends adjusting scan (e.g., acquisition) parameters and reduce the risk of the user "losing" the feature of interest while attempting to control the volume rate. This may reduce exam time and/or improve diagnostic quality of images acquired in some applications.

An ultrasound system according to the present disclosure may utilize an artificial neural network (referred to simply as a neural network), for example a deep neural network (DNN), a convolutional neural network (CNN), a recurrent neural network (RNN), an autoencoder neural network, or the like, to automatically detect features of interest in a scanned volume. In various examples, the neural network(s) may be trained using any of a variety of currently known or later developed learning techniques to obtain a neural network (e.g., a trained algorithm or hardware-based system of nodes) that is configured to analyze input data in the form of ultrasound image frames, measurements, and/or statistics and determine whether a feature of interest is present in a plane or volume. Based on the output of the neural network, the ultrasound system may set and/or adjust scan parameters to set the scanned volume to more closely match the volume of the feature of interest.

An ultrasound system in accordance with principles of the present invention may include or be operatively coupled to an ultrasound transducer configured to transmit ultrasound pulses toward a medium, e.g., a human body or specific portions thereof, and generate echo signals responsive to the ultrasound pulses. The ultrasound system may include a beamformer configured to perform transmit and/or receive beamforming, and a display configured to display, in some examples, ultrasound images generated by the ultrasound imaging system. The ultrasound images may be two-dimensional images or 3-dimensional images (e.g., renders). The ultrasound imaging system may include one or more processors and at least one model of a neural network, which may be implemented in hardware and/or software components. The neural network can be trained to determine whether a feature of interest is present in a scanned volume or plane.

The neural network implemented according to the present disclosure may be hardware—(e.g., neurons are represented by physical components) or software-based (e.g., neurons and pathways implemented in a software application), and can use a variety of topologies and learning algorithms for training the neural network to produce the desired output. For example, a software-based neural network may be implemented using a processor (e.g., single or multi-core Central Processing Unit (CPU), a single Graphics Processing Unit (GPU) or GPU cluster, or multiple processors arranged for parallel-processing) configured to execute instructions, which may be stored in a non-transitory computer readable medium, and which when executed cause the processor to perform a trained algorithm for determining whether a feature of interest is located within a scanned volume. The ultrasound system may include a display or graphics processor, which is operable to arrange the ultrasound images (2D, 3D, 4D etc.) and/or additional graphical information, which may include annotations, user instructions, tissue information, patient information, indicators, color coding, highlights, and other graphical components, in a display window for display on a user interface of the ultrasound system. In some examples, the ultrasound image frames may be provided to a storage and/or memory device, such as a picture archiving and communication system (PACS) for post-exam review, reporting purposes, or future training (e.g., to continue to enhance the performance of the neural network), especially the image frames used to produce items of interest associated with high confidence levels. The display can be remotely located, and interacted with by users other than the sonographer conducting the imaging, in real-time or asynchronously.

FIG. 1 shows an example ultrasound system according to principles of the present disclosure. The ultrasound system 100 may include an ultrasound sensor array 112 configured to transmit ultrasound pulses 114 into a region 116 of a subject, e.g., abdomen, and receive ultrasound echoes 118 responsive to the transmitted pulses as indicated by arrows 10 and 12 respectively. The ultrasound sensor array 112 may be included in a probe (hand-held or affixed) or in a patch (e.g. configured to be adhesively bound to a patient). The region 116 may include one or more features of interest, such as a developing fetus, as shown, or a portion of the developing fetus, such as the heart. Although some illustrative examples may refer to fetuses or fetal anatomy, the teachings of the disclosure are not limited to fetal scans. The region 116 may include a variety of other anatomical objects or portions thereof, such as a kidney or heart, which may be features of interest. As further shown, the ultrasound system 100 can include a beamformer 120, which may control the ultrasound sensor array 112 to scan a volume in the region 116 as indicated by arrow 14. The ultrasound system 100 may include a signal processor 122, which can be configured to generate a stream of discrete ultrasound image frames 124 from the ultrasound echoes 118 received at the array 112 and provided to the signal processor 122 by the beamformer 120 as indicated by arrow 16. The ultrasound image frames 124 may be individually acquired image frames or a part of a sequence, such as a cineloop. Each frame 124 may correspond to an image plane, such as an elevational plane, in the scanned volume of region 116. The image frames 124 may be output by the signal processor 122 and stored in local memory 125 of the system 100 as indicated by arrow 18 where they may be accessed later during an exam or during post-exam review. The local memory 125 may be implemented by one or more hard disk drives, solid-state drives, or any other type of suitable storage device comprising non-volatile memory. In addition to the image frames 124, the local memory 125 may be configured to store additional image data, executable instructions, or any other information necessary for the operation of the system 100.

The image frames 124 can additionally or alternatively be communicated to a data processor 126 as indicated by arrow 20. The data processor 126 may be configured to recognize features of interest and generate scan parameters for scanning an adjusted volume including at least one recognized feature of interest. The data processor 126 may be implemented as one or more microprocessors, graphical processing units, application specific integrated circuit, and/or other processor type. The data processor 126 may receive image frames 124 from the local memory 125 in some applications, for example, during post-exam review. In some examples, the data processor 126 may be configured to recognize features of interest by implementing at least one neural network, such as neural network 128, which can be trained to recognize features of interest in a scanned volume. The data processor 126 may include an acquisition controller 144. The acquisition controller 144 may provide control signals to provide scan parameters to the beamformer 120 and/or ultrasound sensor array 112 as indicated by arrow 22. For example, the acquisition controller 144 may control a number of scan planes, a number of lines per plane, and/or steering of ultrasound beams generated by the ultrasound sensor array 112 and/or beamformer 120. In some applications, the scan parameters may be based, at least in part, on the output of network 128 as indicated by arrow 24. In some examples, the data processor 126 may optionally include multiple processors. For example, network 128 may be included on a first processor 130 and acquisition controller 144 may be included on a second processor 132. In other examples, the network 128 and acquisition controller 144 may be included on a single processor.

In some examples, network 128 may be a static learning network. That is, the network may be fully trained on the system 100 or another system and executable instructions for implementing the fully-trained network 128 are provided to the data processor 126. In other embodiments which are generally equivalent to the static learning network, data processor 126 may be provided with executable instructions which implement functions using similar inputs, which process those inputs in a manner similar to the trained network, and which output similar data.

In some examples, the network 128 may be a dynamic, continuous learning network. In such examples, the executable instructions for implementing the network 128 are modified based on the results of each ultrasound exam. In various examples, the data processor 126 can also be coupled, communicatively or otherwise, to a database 127 as indicated by arrow 26. The database 127 may be configured to store various data types, including executable instructions, training data, and newly acquired, patient-specific data. In some examples, as shown in FIG. 1, the database 127 may be stored on the local memory 125, however, the database 127 may be implemented in a separate storage location on system 100.

The ultrasound system 100 can be configured to acquire ultrasound data from one or more regions of interest 116, which may include an artery, fetus, other anatomy, or features thereof. The ultrasound sensor array 112 may include at least one transducer array configured to transmit and receive ultrasonic energy. The settings of the ultrasound sensor array 112 can be preset for performing a particular scan, and in examples, can be adjustable during a particular scan. A variety of transducer arrays may be used. The number and arrangement of transducer elements included in the sensor array 112 may vary in different examples. The ultrasound sensor array 112 may include a 2D array of transducer elements, corresponding to a matrix array probe. The 2D matrix arrays may be configured to scan electronically in both the elevational and azimuth dimensions (via phased array beamforming) for 2D or 3D imaging. In some examples, the ultrasound sensor array 112 may include a linear (e.g., 1D) or phased array. However, a linear or phased array may only provide control over the width and/or depth dimensions of the scanned volume.

In addition to B-mode imaging, imaging modalities implemented according to the disclosures herein can also include shear-wave and/or Doppler, for example. A variety of users may handle and operate the ultrasound system 100 to perform the methods described herein. In some examples, the user may be an inexperienced, novice ultrasound operator unable to accurately adjust a location and/or dimensions of a volume to be scanned. In some cases, one or more components of the system 100 is controlled by a robot (positioning, settings, etc.), and can replace the human operator data to perform the methods described herein. For instance, the beamformer 120 and/or ultrasound sensor array 112 may be configured to utilize the findings obtained by the data processor 126 to adjust a number of image planes and/or number of lines per plane to set or adjust a volume to be scanned. The adjustment may maintain a feature of interest within the adjusted volume to be scanned. According to such examples, the ultrasound system 100 can be configured to operate in automated fashion by adjusting one or more parameters of the transducer, signal processor, or beamformer in response to feedback received from the data processor 126.

In some examples, the beamformer 120 may comprise a microbeamformer or a combination of a microbeamformer and a main beamformer, coupled to the ultrasound sensor array 112. The beamformer 120 may control the transmission of ultrasonic energy, for example by forming ultrasonic pulses into focused beams. The beamformer 120 may also be configured to control the reception of ultrasound signals such that discernable image data may be produced and processed with the aid of other system components. The role of the beamformer 120 may vary in different ultrasound system varieties. In some examples, the beamformer 120 may comprise two separate beamformers: a transmit beamformer configured to receive and process pulsed sequences of ultrasonic energy for transmission into a subject, and a separate receive beamformer configured to amplify, delay and/or sum received ultrasound echo signals. In some examples, the beamformer 120 may include a microbeamformer operating on groups of sensor elements for other transmit and receive beamforming, coupled to a main beamformer which operates on the group inputs and outputs for both transmit and receive beamforming, respectively. In some examples, the beamformer 120 may receive the scan parameters output by the data processor 126.

The signal processor 122 may be communicatively, operatively and/or physically coupled with the sensor array 112 and/or the beamformer 120. In some examples, the signal processor may be housed together with the sensor array 112 or it may be physically separate from but communicatively (e.g., via a wired or wireless connection) coupled thereto. The signal processor 122 may be configured to receive unfiltered and disorganized ultrasound data embodying the ultrasound echoes 118 received at the sensor array 112. From this data, the signal processor 122 may continuously generate a plurality of ultrasound image frames 124 as a user scans the region of interest 116.

In particular examples, neural network 128 may comprise a deep learning network trained, using training sets of labeled imaging data, to determine when a feature of interest is within the scanned volume or plane. In some examples, the neural network 128 may analyze an image plane for anatomical landmarks to determine if a feature of interest is present in a scanned volume. In some examples, the neural network 128 may analyze two or more orthogonal planes for anatomical landmarks (e.g., A and B planes of a fetal heart). Examples of anatomical landmarks include, but are not limited to, circular or tubular features, which may indicate blood vessels, local intensity maxima, which may indicate an implantable device, and regions of high flow, which may indicate a heart valve. Once a feature of interest has been recognized, the neural network 128 may provide an output to the acquisition controller 144. The output may include a location of the feature of interest and/or dimensions of the feature of interest, which may collectively be referred to as boundary data of the feature of interest.

Based on the output received from the neural network 128, the acquisition controller 144 may determine a variety of scan parameters, for example, a location to scan, a number of imaging planes to acquire, and/or a number of lines per plane to acquire to generate adjusted scan parameters corresponding to a volume or adjusted volume to be scanned. The acquisition controller 144 may output the adjusted scan parameters to the beamformer 120 and/or ultrasound sensor array 112. The adjusted scan parameters output by the acquisition controller 144 may cause the beamformer 120 and/or ultrasound sensor array 112 to adjust the transmitted ultrasound pulses 114 to acquire the number of image planes and lines per plane at locations indicated by the adjusted scan parameters. In some applications, the adjusted volume acquired by ultrasound sensor array 112 may be smaller than the initial volume scanned. Thus, the volume rate may be increased while still imaging the feature of interest in some applications.

Figure 2:
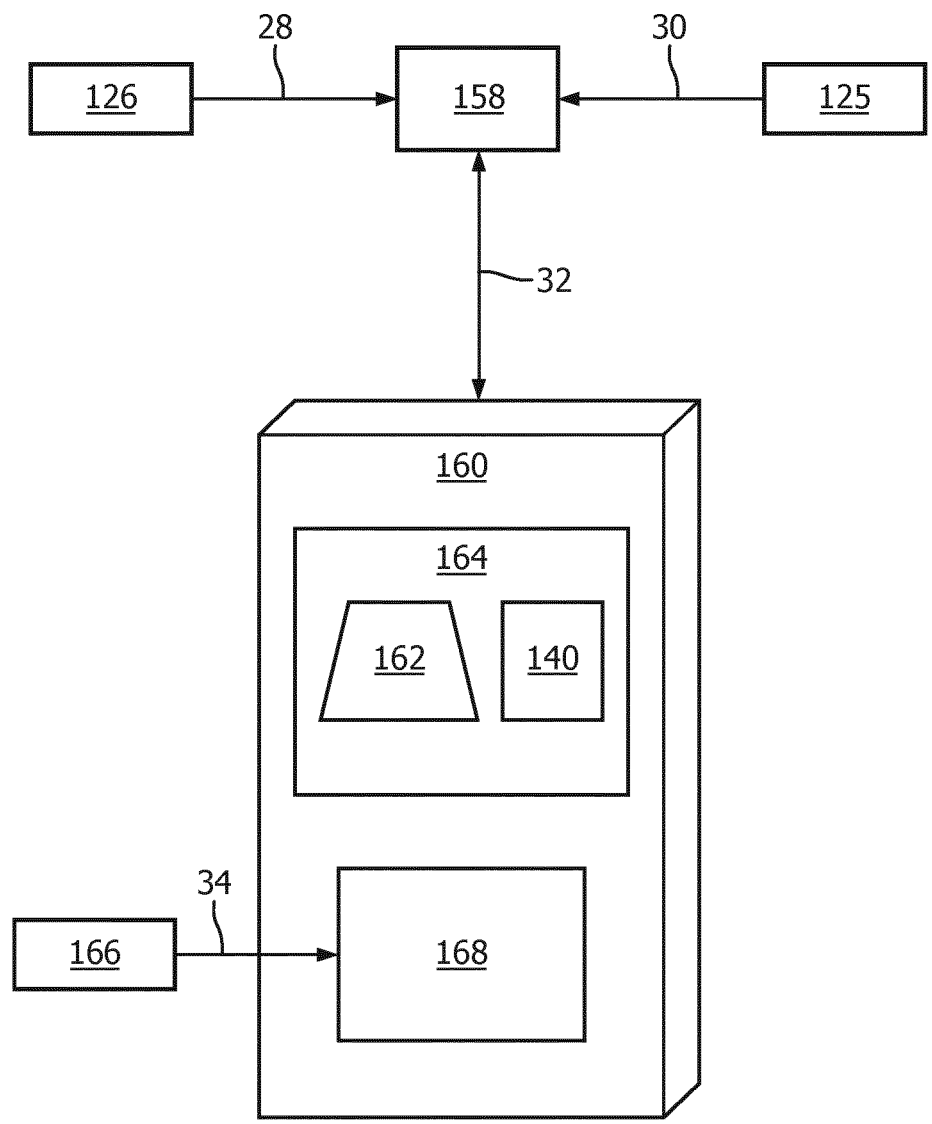
FIG. 2 is a diagram showing additional components of the ultrasound system of FIG. 1.

FIG. 2 shows additional components of the system 100. As discussed above, one or more acquired ultrasound image frames can be displayed to a user via one or more components of system 100. As shown in FIG. 2, such components can include a display processor 158 communicatively coupled with data processor 126 as indicated by arrow 28. The display processor 158 is further coupled with a user interface 160 as indicated by arrow 32, such that the display processor 158 can link the data processor 126 (and thus the one or more neural networks and acquisition controller operating thereon) to the user interface 160, enabling the data processor outputs to be displayed on a display 164 of the user interface 160. For example, 2D planes and/or 3D volumes may be displayed. The 2D planes and/or 3D volumes displayed may be based on the volume initially scanned by the user and/or the volume scanned based on the scan parameters generated by the acquisition controller 144. The display 164 may include a display device implemented using a variety of known display technologies, such as Liquid-Crystal Display (LCD), Light-Emitting Diode (LED), Organic Light-Emitting Diode (OLED), or plasma display technology. In some examples, the display processor 158 can be configured to generate ultrasound images 162 from the image frames 124 received at the data processor 126 and/or local memory 125 as indicated by arrow 30. In some examples, the user interface 160 can be configured to display the ultrasound images 162 in real time as an ultrasound scan is being performed. In some examples, user display 164 may comprise multiple displays. In some examples, the ultrasound images 162 may be displayed on a first display 164 and user interface options may be displayed on a second display 164 concurrently.

The user interface 160 can also be configured to receive a user input 166 via a user control or controls 168 at any time before, during, or after an ultrasound scan as indicated by arrow 34. For instance, the user interface 160 may be interactive, receiving user input 166 indicating a desired exam type and/or feature of interest. In some examples, the desired exam type and/or feature of interest may be provided to the neural network 128. In these examples, the neural network 128 may search for particular features of interest based on the exam type or feature of interest indicated by the user. In some examples, the input 166 may include an adjustment one or more imaging settings (e.g., gain). In some examples, the user control(s) 168 may include one or more hard controls (e.g., buttons, knobs, dials, encoders, mouse, trackball or others). In some examples, the user control(s) 168 may additionally or alternatively include soft controls (e.g., GUI control elements or simply, GUI controls) provided on a touch sensitive display. In some examples, display 164 may be a touch sensitive display that includes one or more soft controls 140 of the user control(s) 168.

The configuration of the components shown in FIG. 2, along with FIG. 1, may vary. For example, the system 100 can be portable or stationary. Various portable devices, e.g., laptops, tablets, smart phones, remote displays and interfaces, or the like, may be used to implement one or more functions of the system 100. The physical configuration of the components shown in FIGS. 1-2 may vary. For example, the ultrasound sensor array 112, beamformer 120, signal processor 122, memory 125, and data processor 126 may be included in an ultrasound probe and the user interface 160 and display 158 may be included in a separate computing device (e.g., ultrasound base system, laptop, tablet). The ultrasound probe and computing device may be physically (e.g., cable) or wirelessly coupled. In another example, the ultrasound sensor array 112 is included in an ultrasound probe and all of the other components of system 100 are included in a base unit of an ultrasound imaging system. The ultrasound probe may be physically or wirelessly coupled to the base unit. Other physical configurations may also be used.

Some or all of the data processing may be performed remotely, (e.g., in the cloud). In examples that incorporate such devices, the ultrasound sensor array 112 may be connectable via a USB interface, for example. In some examples, various components shown in FIGS. 1 and 2 may be combined. For instance, neural network 128 may be merged with the acquisition controller 144. According to such examples, the output generated by neural network 128 may still be input into acquisition controller 144, but the network and controller may constitute sub-components of a larger, layered network, for example. In some examples, various components shown in FIGS. 1 and 2 may include multiple components. For example, signal processor 122 may include multiple processors (e.g., Doppler processor, B-mode processor, scan converter, multiplanar reformatter, volume renderer).

In some examples, the system 100 can be configured to implement neural network 128, which may include a CNN, to determine when a feature of interest is located in a scanned volume or plane. In some examples, neural network 128 may include multiple neural networks. The neural network 128 may be trained with imaging data such as image frames where one or more features of interest are labeled as present. Neural network 128 may be trained to recognize target anatomical features associated with standard ultrasound exams (e.g., different standard views of the heart for echocardiography) or a user may train neural network 128 to locate one or more custom target anatomical features (e.g., implanted device, liver tumor).

In some examples, a neural network training algorithm associated with the neural network 128 can be presented with thousands or even millions of training data sets in order to train the neural network to determine when at least one feature of interest is present in a scanned volume or plane. In various examples, the number of ultrasound images used to train the neural network(s) may range from about 50,000 to 200,000 or more. The number of images used to train the network(s) may be increased if higher numbers of different items of interest are to be identified, or to accommodate a greater variety of patient variation, e.g., weight, height, age, etc. The number of training images may differ for different features of interest or sub-features thereof, and may depend on variability in the appearance of certain features. For example, tumors typically have a greater range of variability than normal anatomy. In another example, fetal hearts may vary as the development of the fetus progresses. Training the network 128 to assess the presence of items of interest associated with features for which population-wide variability is high may necessitate a greater volume of training images.

Figure 3:
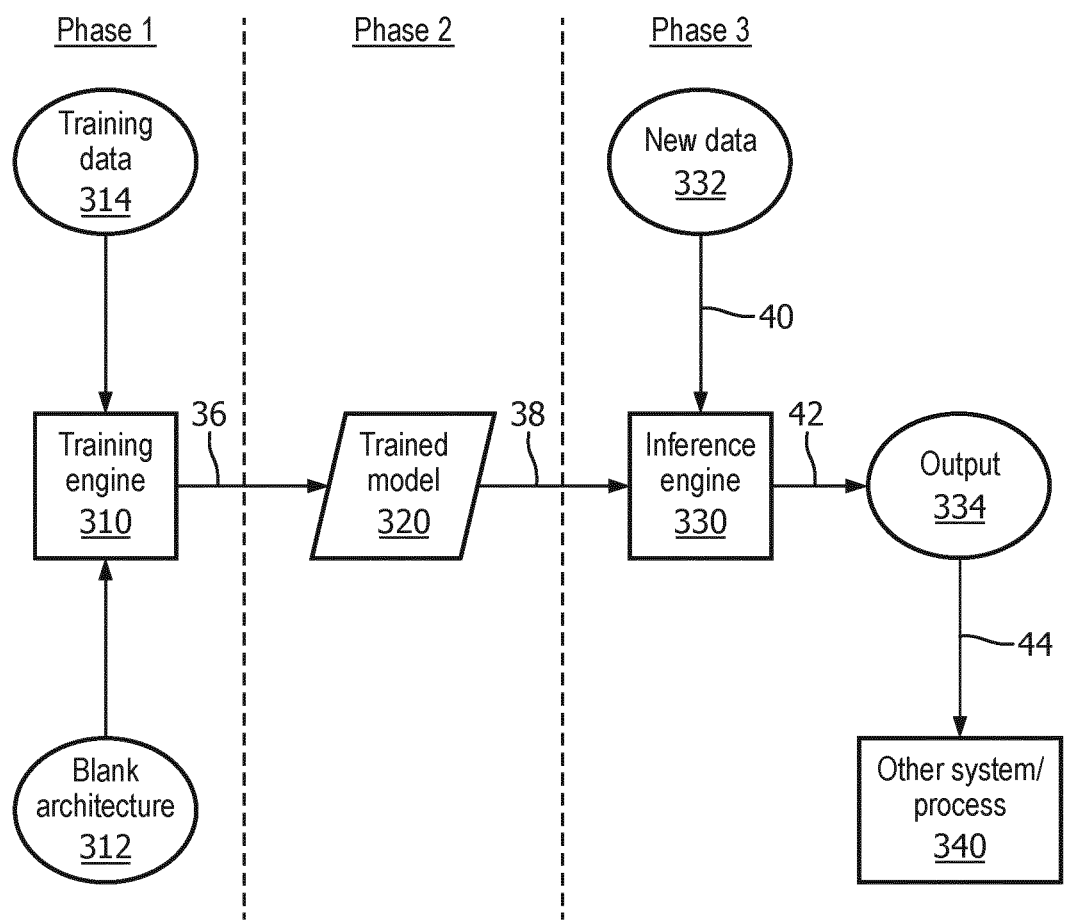
FIG. 3 shows a block diagram of a process for training and deployment of a neural network in accordance with examples described herein.

FIG. 3 shows a block diagram of a process for training and deployment of a neural network in accordance with the principles of the present disclosure. The process shown in FIG. 3 may be used to train network 128. The left hand side of FIG. 3, phase 1, illustrates the training of a neural network. To train neural network 128, training sets which include multiple instances of input arrays and output classifications may be presented to the training algorithm(s) of the neural network(s) (e.g., AlexNet training algorithm, as described by Krizhevsky, A., Sutskever, I. and Hinton, G. E. "ImageNet Classification with Deep Convolutional Neural Networks," NIPS 2012 or its descendants). Training may involve the selection of a starting network architecture 312 and the preparation of training data 314. The starting network architecture 312 may be a blank architecture (e.g., an architecture with defined layers and arrangement of nodes but without any previously trained weights) or a partially trained network, such as the inception networks, which may then be further tailored for classification of ultrasound images. The starting architecture 312 (e.g., blank weights) and training data 314 are provided to a training engine 310 for training the model as indicated by arrow 36. Upon sufficient number of iterations (e.g., when the model performs consistently within an acceptable error), the model 320 is said to be trained and ready for deployment, which is illustrated in the middle of FIG. 3, phase 2. The right hand side of FIG. 3, or phase 3, the trained model 320 is applied (via inference engine 330 as indicated by arrow 38) for analysis of new data 332 as indicated by arrow 40, which is data that has not been presented to the model during the initial training (in phase 1). For example, the new data 332 may include unknown images such as live ultrasound images acquired during a scan of a patient (e.g., image frames 124 in FIG. 1). The trained model 320 implemented via engine 330 is used to classify the unknown images in accordance with the training of the model 320 to provide an output 334 (e.g., boundary data for a feature of interest present in a scanned volume) as indicated by arrow 42. The output 334 (e.g., dimensions and location within the scanned volume of a feature of interest) may then be used by the system for subsequent processes 340 (e.g., as input to one or more other machine-learning models as indicated by arrow 44, and for effecting an action by the system 100 such as generating scan parameters for scanning an adjusted volume with the feature of interest).

In the examples where the trained model 320 is used to implement neural network 128, the starting architecture may be that of a convolutional neural network, or a deep convolutional neural network, which may be trained to perform image frame indexing, image segmentation, image comparison, or any combinations thereof. With the increasing volume of stored medical image data, the availability of high-quality clinical images is increasing, which may be leveraged to train a neural network to learn to determine when a feature of interest is present in a scanned volume. The training data 314 may include multiple (hundreds, often thousands or even more) annotated/labeled images, also referred to as training images. It will be understood that the training image need not include a full image produced by an imagining system (e.g., representative of the full field of view of the probe) but may include patches or portions of images of the labeled item of interest.

In various examples, the trained neural network 128 may be implemented, at least in part, in a computer-readable medium comprising executable instructions executed by a processor, e.g., data processor 126.

Figure 4:
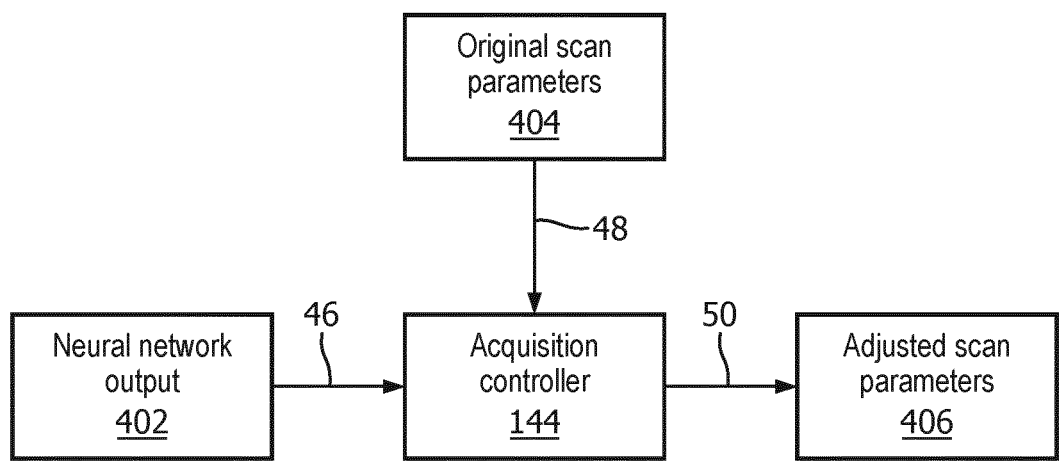
FIG. 4 is a block diagram of inputs and outputs of the acquisition controller 144 in accordance with examples described herein.

FIG. 4 is a block diagram of inputs and outputs of the acquisition controller 144 in accordance with examples described herein. The acquisition controller 144 may receive an output 402 from the neural network 128 (e.g., output 334 shown FIG. 3) as indicated by arrow 46. The output may include boundary data such as dimensions and location of a feature of interest. Optionally, the acquisition controller 144 may receive original scan parameters 404 used to initially scan a volume or plane in the region 116 as indicated by arrow 48. The original scan parameters may be received from the beamformer 120 and/or ultrasound sensor array 112. The acquisition controller 144 may use the inputs 402 and 404 to generate adjusted scan parameters 406 as indicated by arrow 50. The adjusted scan parameters 406 may include beamformer variables such as which transducer elements of the transducer array to activate, when to activate the transducer elements, and/or delays to apply to each channel of the beamformer and/or microbeamformer. The adjusted scan parameters 406 may be provided to the beamformer 120 and/or ultrasound sensor array 112. The adjusted scan parameters 406 may cause the ultrasound sensor array 112 to scan an adjusted volume that includes the feature of interest. By adjusting the volume scanned by the ultrasound sensor array 112, the acquisition controller 144 may control the volume rate in some applications.

Figure 5:
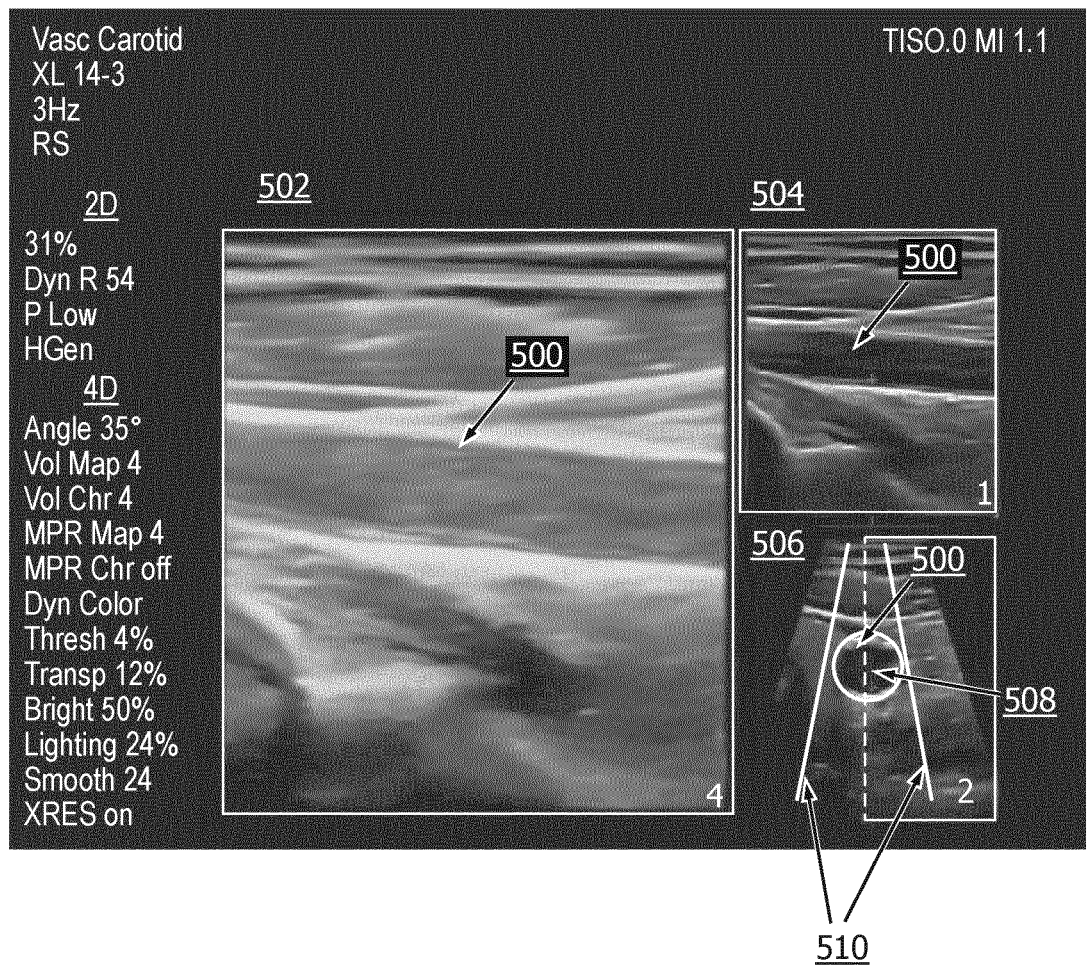
FIG. 5 shows representative ultrasound images of scanned volumes in accordance with examples described herein.
Figure 5:
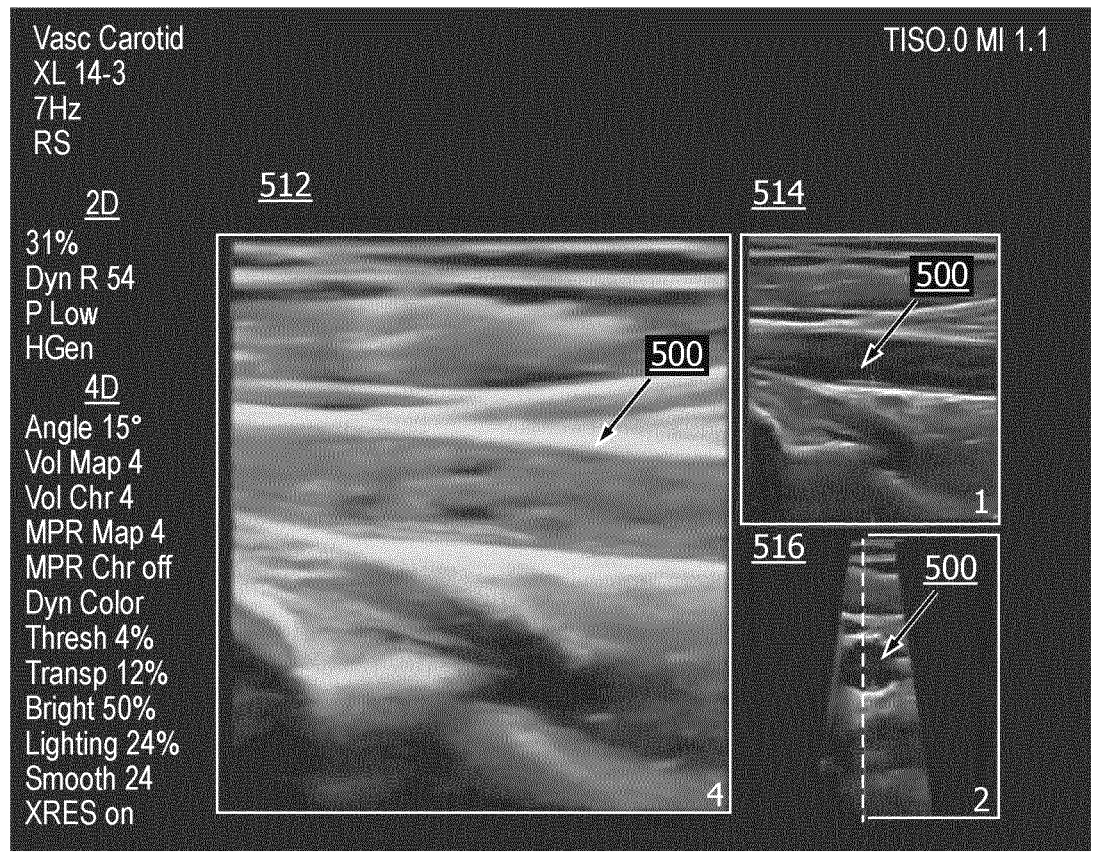

FIG. 5 shows representative ultrasound images of scanned volumes in accordance with examples described herein. Pane 502 is a 3D ultrasound image of a portion of a carotid artery 500 in an initially scanned volume. Pane 504 is a 2D image of longitudinal plane of the portion of the carotid artery 500. Pane 506 is a 2D image of a transverse plane of the portion of the carotid artery 500. In some examples, the longitudinal and transverse planes may have been extracted from the 3D volume by a multiplanar reformatter. In the example shown in FIG. 5, the neural network 128 analyzed the transverse plane shown in pane 506 and determined the carotid artery 500 (e.g., the feature of interest) was present in the scanned volume as indicated by the circle 508. The neural network 128 provided boundary data of the carotid artery 500 to the acquisition controller 144. Based on the boundary data, the acquisition controller 144 generated adjusted scan parameters. In this example, the adjusted scan parameters correspond to an adjusted elevational angle, as indicated by lines 510. In this example, the adjusted elevational angle is narrower than the elevational angle of the initially scanned volume.

Pane 512 is a 3D ultrasound image of a portion of the carotid artery 500 in the adjusted volume. Pane 514 is a 2D image of longitudinal plane of the portion of the carotid artery 500 in the adjusted volume. Pane 506 is a 2D image of a transverse plane of the portion of the carotid artery in the adjusted volume. As can be seen most notably in pane 516, the adjusted volume more closely aligns with a volume of the carotid artery 500. Thus, less "extraneous" tissue around the carotid artery 500 is scanned. The reduction in scanned volume of the adjusted volume compared to the initially scanned volume may provide for an increase in volume rate. In the example shown in FIG. 5, the volume rate increased from 3 Hz to 7 Hz.

In some applications, a user may acquire one or more 2D planes in a volume prior to scanning the entire volume. In these applications, the ultrasound imaging system may determine a volume to scan based, at least in part, on the neural network's analysis of the one or more 2D planes.

Figure 6:
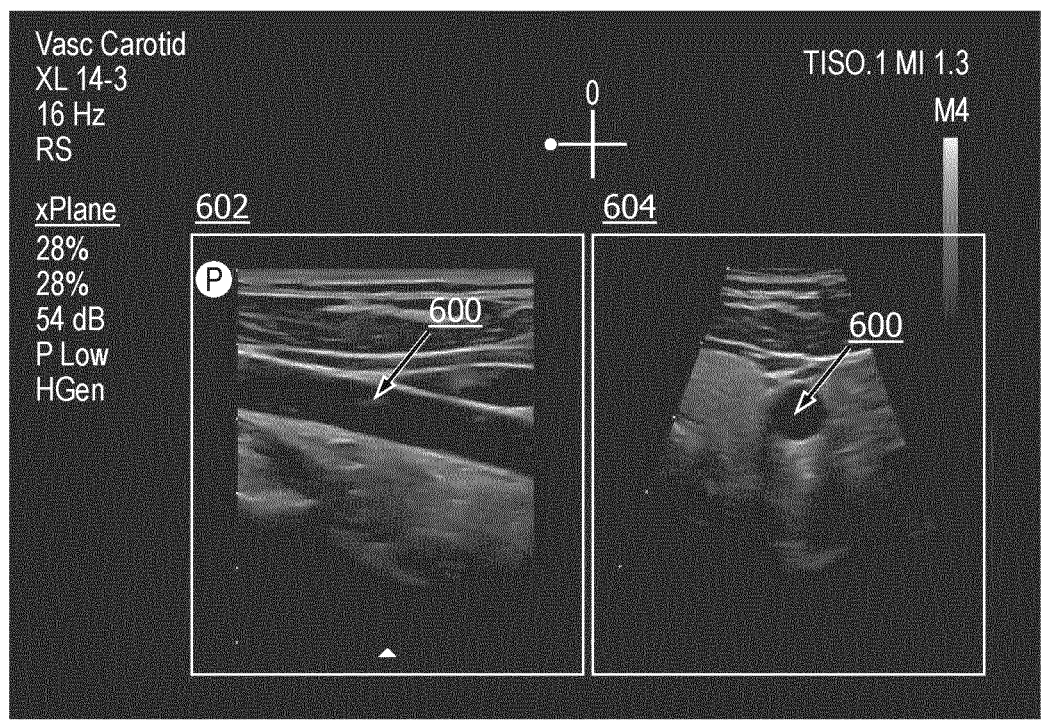
FIG. 6 shows representative ultrasound images in accordance with examples described herein.
Figure 6:
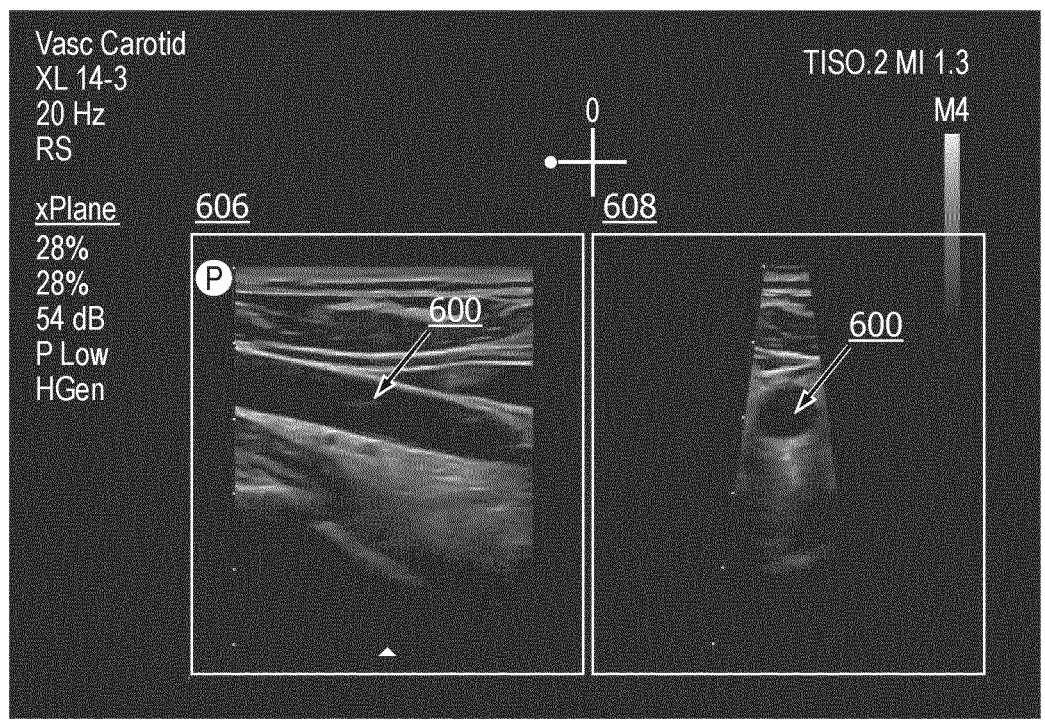

FIG. 6 shows representative ultrasound images in accordance with examples described herein. Pane 602 is a 2D image of longitudinal plane of a portion of the carotid artery 600. Pane 604 is a 2D image of a transverse plane of the portion of the carotid artery 600. In the example shown in FIG. 6, the neural network 128 may analyze pane 602 and/or 604 and determine the carotid artery 600 is present and generate boundary data for the carotid artery 600 (e.g., the feature of interest). The boundary data may be provided to the acquisition controller 144, which may generate adjusted scan parameters that define a volume to be scanned. Pane 606 is a 2D image of longitudinal plane of a portion of the carotid artery 600 based on the adjusted scan parameters. Pane 608 is a 2D image of a transverse plane of the portion of the carotid artery 600 based on the adjusted scan parameters. Although still only acquiring 2D planes, the adjusted scan parameters have increased the frame rate from 16 Hz to 20 Hz. A volume scanned based on the adjusted scan parameters may have a higher volume rate than a volumes scanned based on the initial scan parameters used to acquire the images shown in panes 602 and 604.

In some examples, the ultrasound imaging system may adjust the scan parameters in multiple planes, not just a single plane, such as the transverse plane.

Figure 7:
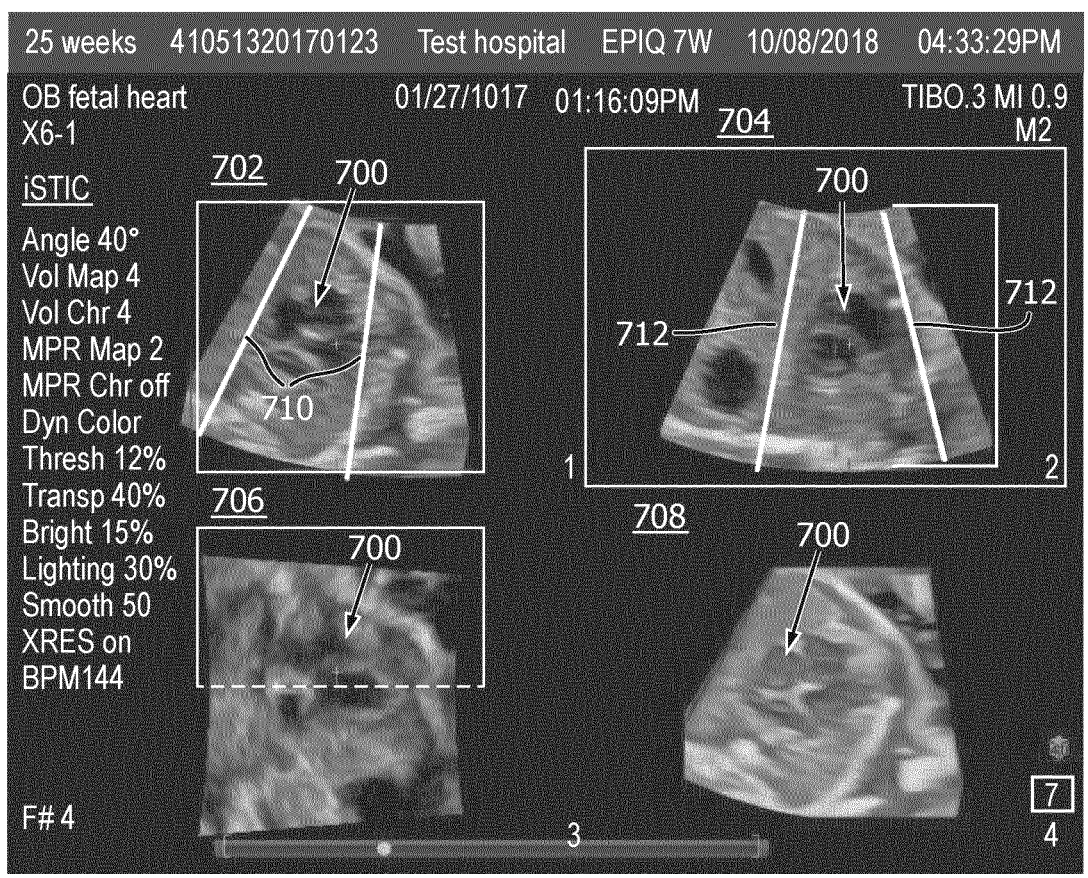
FIG. 7 shows representative ultrasound images of scanned volumes in accordance with examples described herein.

FIG. 7 shows representative ultrasound images of scanned volumes in accordance with examples described herein. Panes 702, 704, and 706 show various 2D images of a fetal heart 700. Pane 708 is a 3D image of the fetal heart 700. In the example shown in FIG. 7, the neural network 128 may analyze pane 702, 704, and/or 706 to determine the fetal heart 700 is present and generate boundary data for the fetal heart 700 (e.g., the feature of interest). The boundary data may be provided to the acquisition controller 144, which may generate adjusted scan parameters that define a volume to be scanned. In the example shown in FIG. 7, the adjusted scan parameters may reduce the sector width as shown by lines 710 in pane 702 and reduce the elevational angle as shown by lines 712 in pane 704. A volume scanned including the fetal heart 700 based on the adjusted scan parameters may be scanned at a faster rate (e.g., higher volume rate) than the initially scanned volume shown in FIG. 7. In some applications, the higher volume rate may allow better visualization of the movement of the fetal heart 700.

Figure 8:
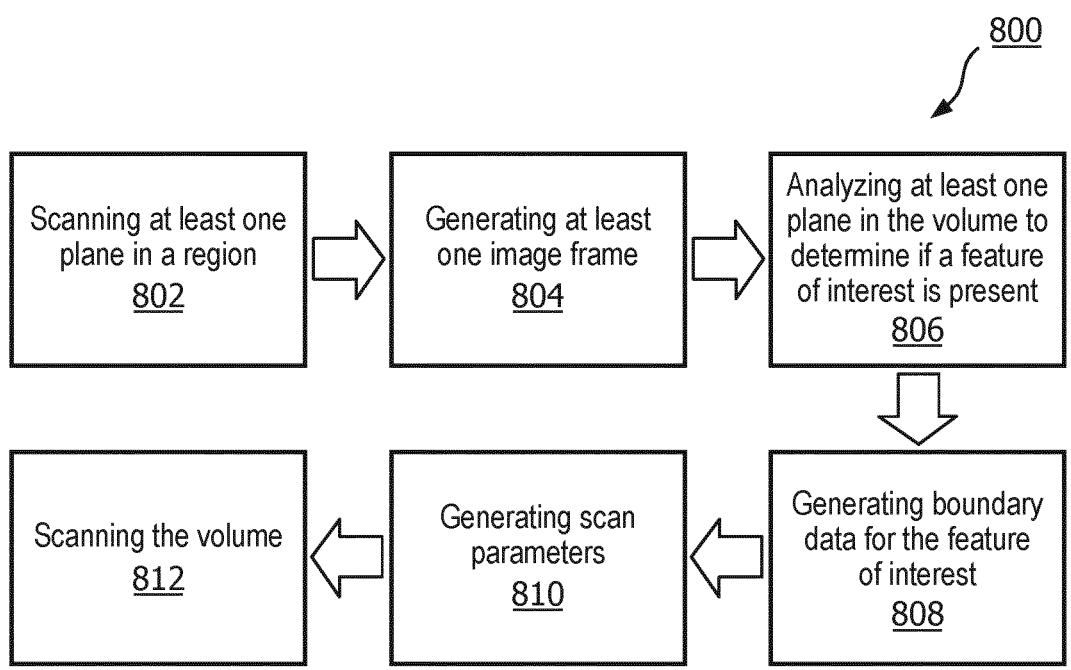
FIG. 8 is a flow chart of a method in accordance with examples described herein.

FIG. 8 is a flow chart 800 of a method in accordance with some examples of the present disclosure. For example, the method of flow chart 800 may be performed as illustrated in FIGS. 5-7 in some applications. At block 802, a step of "scanning at least one plane in a region," may be performed. In some examples, scanning may be performed by an ultrasound sensor array 112. In some examples, the ultrasound sensor array 112 may be controlled by a beamformer 120. At block 804, a step of "generating at least one image frame" may be performed. The at least one image frame may be generated from the scanning of the at least one plane in some examples. In some examples, the at least one image frame may be generated by a signal processor 122. At block 806, a step of "analyzing at least one plane to determine if a feature of interest is present," may be performed. In some examples, the analyzing may be performed by a neural network 128, which may in some examples be included in a data processor 126. In some examples, the neural network 128 may be trained to search for anatomical landmarks to determine if the feature of interest is present. If the feature of interest is determined to be present at block 806, at block 808, a step of "generating boundary data for the feature of interest," may be performed. In some examples, the generating may be performed by the neural network 128. At block 810, a step of "generating scan parameters" may be performed. In some examples, the generating may be performed by an acquisition controller 144. In some examples, the acquisition controller 144 may be included with the data processor 126. The scan parameters may correspond to a volume that includes the feature of interest and be based at least in part on the boundary data provided by the neural network 128. At block 812, a step of "scanning the volume" may be performed. In some examples, the scanning may be performed by the ultrasound sensor array 112. In some examples, the adjusted volume may be provided on a display.

The systems and methods described herein may provide improvements to the functioning of an ultrasound imaging system in some applications. For example, the systems and methods described herein may allow for automatic and/or semi-automatic adjustment of dimensions of a volume and/or volume rate of acquisition of the ultrasound imaging system. This may reduce the amount of time required by a user to adjust settings on the ultrasound imaging system manually. This may further reduce the risk that the user will lose a feature of interest within a scanned volume while adjusting a volume scanned by the ultrasound imaging machine.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "C#", "Java", "Python", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound imaging system comprising:
a signal processor configured to receive ultrasound signals via an ultrasound sensor array, the ultrasound signals corresponding to at least one imaging plane including a first plane and a second plane orthogonal to the first plane in a region, and to generate at least one image frame from the at least one plane comprising an image frame corresponding to the first plane and a second image frame corresponding to the second plane;
a data processor in communication with the signal processor, wherein the data processor is configured to receive the at least one image frame and output boundary data for a feature of interest responsive to a determination that the feature of interest is present in the at least one image frame, wherein the data processor is configured to determine the boundary data by analyzing, using a neural network, the first plane, the second plane, or both the first plane and the second plane,
and wherein the data processor further includes an acquisition controller configured to receive the boundary data, and generate, using the boundary data, scan parameters corresponding to a volume including the feature of interest; and
a beamformer in communication with the data processor, wherein the beamformer is configured to receive the scan parameters and cause the ultrasound sensor array to perform subsequent scanning of the volume including the feature of interest in accordance with the scan parameters.

2. The ultrasound imaging system of claim 1, wherein the scan parameters include at least one of;
a number of imaging planes,
a number of lines per imaging plane, and
an elevational angle.

3. The ultrasound imaging system of claim 1, wherein the data processor includes a first processor including the neural network and a second processor including the acquisition controller.

4. The ultrasound imaging system of claim 1, wherein a volume rate for the volume is greater than a volume rate for the region.

5. The ultrasound imaging system of claim 1, further comprising a user interface configured to receive a user input via a user control, wherein the user input is provided to the neural network, wherein the user input defines a plurality of features of interest analyzed by the neural network to determine if the feature of interest is present.

6. The ultrasound imaging system of claim 5, wherein the user input corresponds to an exam type.

7. The ultrasound imaging system of claim 5, wherein the user input corresponds to a type of feature of interest.

8. The ultrasound imaging system of claim 1, further comprising a display configured to display at least one of a three dimensional image or a two dimensional image of the volume.

9. The ultrasound imaging system of claim 1, wherein the neural network comprises a layered network, and wherein the acquisition controller comprises a subcomponent of the layered network.

10. The ultrasound imaging system of claim 1, wherein the neural network is trained, using training data, to identify a plurality of features of interest, wherein the training data comprises a plurality of image frames corresponding to a respective plurality of imaging planes, and wherein the respective plurality of imaging planes include at least some orthogonal planes.

11. A method comprising:
   scanning, with an ultrasound sensor array, at least one plane including a first plane and a second plane orthogonal to the first plane in a region;
   generating at least one image frame from the at least one plane;
   analyzing, with a neural network of a data processor, the at least one image frame comprising an image frame corresponding to the first plane and a second image frame corresponding to the second plane to determine if a feature of interest is present;
   generating, with the neural network and responsive to a determination that the feature of interest is present in the at least one image frame, boundary data for the feature of interest, wherein the boundary data is generated based on analyzing, using the neural network, the first plane, the second plane, or both the first plane and the second plane;
   generating, with an acquisition controller of the data processor and responsive to the determination that the feature of interest is present in the at least one image frame, scan parameters corresponding to a volume that includes the feature of interest, based at least in part on the boundary data; and
   scanning, with the ultrasound sensor array, the volume.

12. The method of claim 11, wherein the boundary data includes at least one of, a dimension or a location of the feature of interest.

13. The method of claim 11, further comprising receiving, via a user interface, a user input indicating a type of exam or a desired feature of interest.

14. The method of claim 11, wherein the scan parameters include at least one of:
   a number of imaging planes,
   a number of lines per imaging plane, and
   an elevational angle.

15. The method of claim 14, wherein the imaging planes are spaced according to the elevational angle, such that a distance between respective centers of successive ones of the imaging planes is constant, and/or wherein a density of the lines is held constant.

16. The method of claim 11, wherein the feature of interest is based on a user input.

17. A non-transitory computer readable medium including executable instructions, that when executed, cause an ultrasound imaging system to perform the method of claim 11.

* * * * *